United States Patent [19]

Ulrich

[11] Patent Number: 5,177,811
[45] Date of Patent: Jan. 12, 1993

[54] FLEXIBLE VISOR-LIKE HEAD COVERING

[76] Inventor: Jan Ulrich, 1039 S. Parker Rd., Apartment No. 2F, Denver, Colo. 80231

[21] Appl. No.: 816,331

[22] Filed: Dec. 31, 1991

Related U.S. Application Data

[63] Continuation-in-part of Ser. No. 650,236, Feb. 4, 1991, Pat. No. 5,121,506.

[51] Int. Cl.⁵ .............................................. A42B 1/20
[52] U.S. Cl. ........................................ 2/177; 2/175; 2/195; 2/196
[58] Field of Search ............... 2/12, 171, 171.4, 171.5, 2/171.7, 171.8, 175, 177, 178, 195, 196, 209.1

[56] References Cited

U.S. PATENT DOCUMENTS

| | | | |
|---|---|---|---|
| 351,466 | 10/1886 | Robbins . | |
| 480,041 | 8/1892 | Schlesinger | 2/175 |
| 553,043 | 1/1896 | Samuels | 2/195 |
| 971,503 | 9/1910 | Howard . | |
| 1,435,533 | 11/1922 | Knackstedt | 2/12 |
| 21,495,041 | 1/1950 | Weiss | 2/209.1 |
| 1,558,142 | 10/1925 | Brenner . | |
| 1,636,889 | 7/1927 | Wittcoff . | |
| 1,666,098 | 4/1928 | Kaul | 2/195 |
| 2,007,235 | 7/1935 | Woodside | 2/175 |
| 2,149,468 | 3/1939 | Santise | 2/198 |
| 2,681,451 | 6/1954 | Lipschutz | 2/195 |
| 2,845,289 | 7/1958 | Cicogna | 287/77 |
| 2,931,046 | 4/1960 | Klein | 2/195 |
| 3,357,026 | 12/1967 | Wiegandt | 2/195 |
| 4,096,590 | 6/1978 | Keshock | 2/180 |
| 4,097,934 | 7/1978 | Weinstein | 2/195 |
| 4,556,993 | 12/1985 | Okamura | 2/196 |
| 4,610,038 | 9/1986 | Dennard | 2/196 |
| 4,741,053 | 5/1988 | Okamura | 2/196 |
| 4,856,117 | 8/1989 | Goldman | 2/195 |
| 4,999,851 | 3/1991 | Hall | 2/175 |
| 5,121,506 | 6/1992 | Ulirch | 2/171.5 |

FOREIGN PATENT DOCUMENTS

| | | | |
|---|---|---|---|
| 3627 | 7/1900 | Austria | 2/195 |
| 787503 | 9/1935 | France | 2/196 |
| 968542 | 11/1950 | France | 2/177 |
| 995629 | 12/1951 | France | 2/177 |
| 255391 | 1/1949 | Switzerland | 2/177 |
| 275147 | 5/1951 | Switzerland | 2/177 |
| 187553 | 10/1922 | United Kingdom | 2/195 |
| 433835 | 8/1935 | United Kingdom | 2/177 |

Primary Examiner—Werner H. Schroeder
Assistant Examiner—Diana L. Biefeld
Attorney, Agent, or Firm—John E. Reilly

[57] ABSTRACT

A head covering is in the form of a visor-like cap having an upper band or head-encircling portion with a wire reinforcing member around its upper edge and a visor extending downwardly from the band which includes a crescent-shaped section and a wire reinforcing member embedded in the outer peripheral edge of the crescent-shaped section so as to cause the cap to assume the desired configuration when worn and when not worn to permit it to be coiled into a compact package for storage purposes.

12 Claims, 1 Drawing Sheet

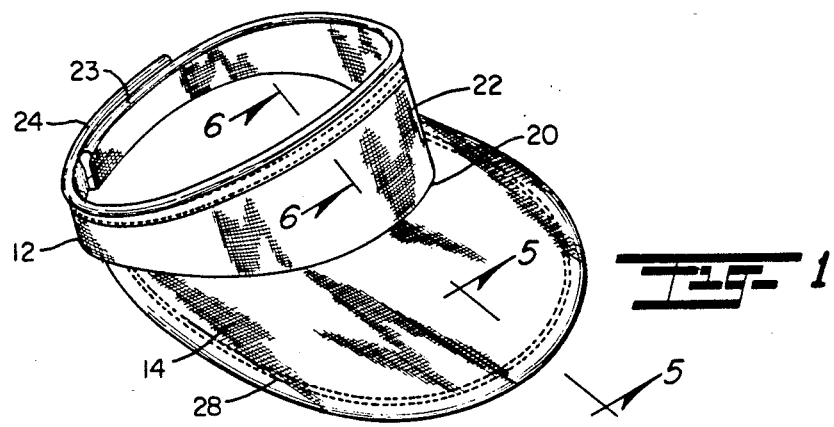
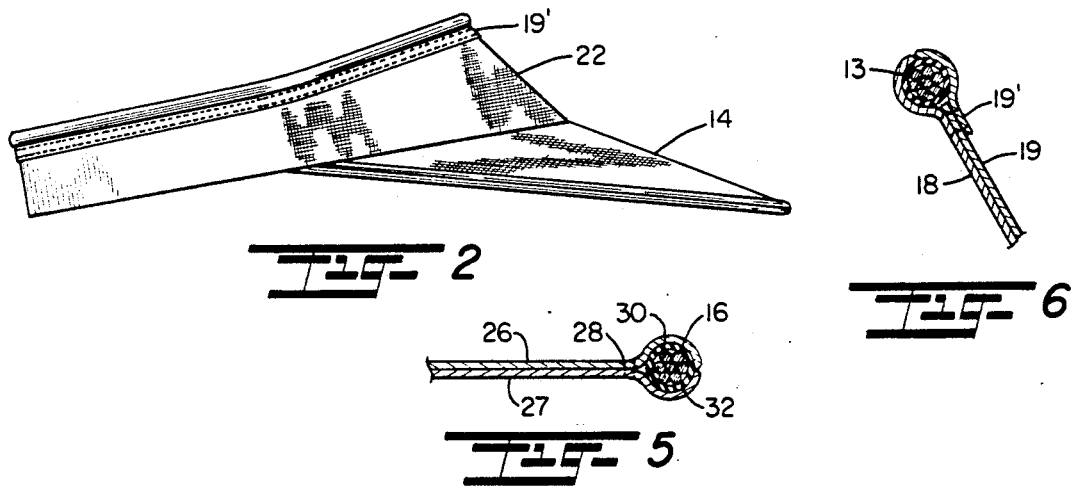
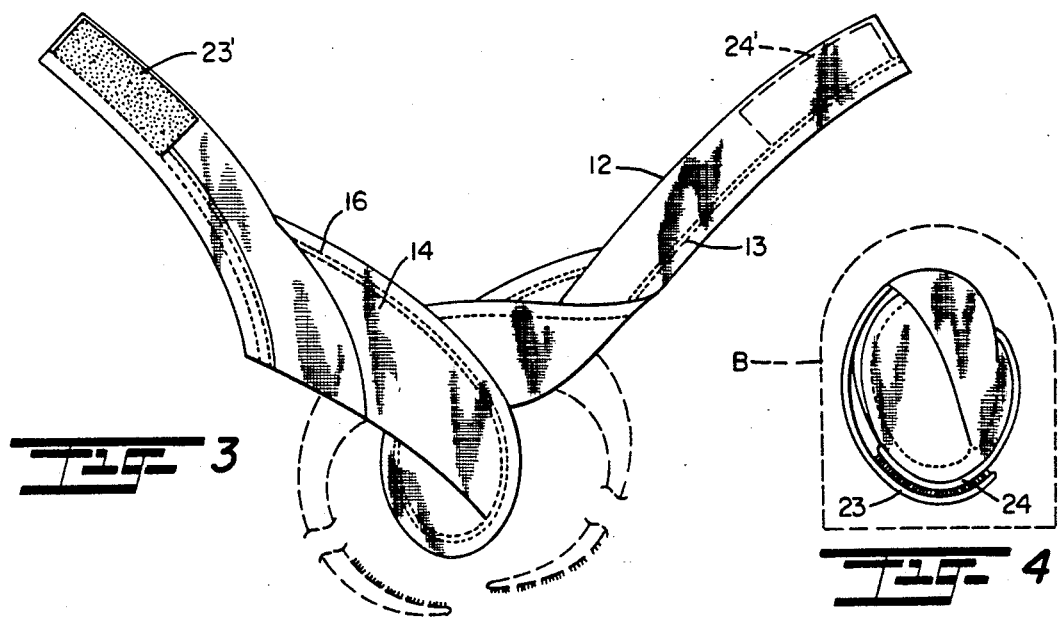

FLEXIBLE VISOR-LIKE HEAD COVERING

CROSS-REFERENCE TO RELATED APPLICATIONS

This application is a continuation-in-part application of Ser. No. 650,236 filed Feb. 4, 1991 for COLLAPSIBLE VISOR-LIKE HEAD COVERING, invented by the inventor of the present application, now U.S. Pat. No. 5,121,506.

This invention relates to headwear; and more particularly relates to a novel and improved visor-like cap or hat which can be coiled into a compact condition for convenient storage when not in use.

BACKGROUND AND FIELD OF THE INVENTION

Visor-like caps are in widespread use for various outdoor activities as a sunshade or screen. For instance, they are almost exclusively used by baseball players and by a great number of golfers and tennis players. Typically, the caps are subjected to an extreme amount of abuse, wear and tear as well as being deformed out of their proper configuration when laundered or folded into one's pocket or stuffed into a golf bag pocket. Under repeated use, conventional caps tend to become misshapen and this is especially true of the more popular form of visor in which the entire bill is reinforced with a cardboard or cardboard-like material which when folded or severely bent will not very easily return to its original curved configuration.

It has been proposed in the past to devise full-brimmed hats with outer wire or wire-like reinforcing members along their brims which can be coiled into a compact condition for storage purposes. Typically, such hats have required the use of some form of special material, such as, a fabric having directional strength or a particular dimensional relationship between the size of the brim and size of the reinforcing member. In this relation, it is desirable that the upper head-encircling portion be reinforced with a wire or wire-like member in such a way as to permit coiling into a compact storage condition as described; and when uncoiled and placed on the head will restore the upper portion of the cap to its original configuration.

Visor-like cap constructions have been devised with deformable reinforcing wires but are not designed in such a way that the cap can be coiled into a compact storage condition so as not to become misshapen when not in use; yet, when uncoiled, the visor will automatically spring back into its original crescent-shaped configuration with a curved bill when placed on the head of the wearer. Representative patents disclosing visor-like cap constructions with a reinforcing or stiffener section are U.S. Pat. Nos. 2,931,046 to H. D. Klein, 1,666,098 to G. P. Kaul, 971,503 to C. I. Howard, 351,466 to J. J. Robbins and 1,435,533 to L. C. Knackstedt. Other foreign patents of interest are British Patent No. 187,553 to W. Schwalbe and Austrian Patent No. 3,627 to J. Komrowsky. A patent of particular interest in this regard is U.S. Pat. No. 3,357,026 to R. C. Wiegandt in which a resilient stay or wire is designed to reinforce and lend a specific shape to the bill of a cap without utilizing a cardboard or similar material in the bill itself. However, in Weigandt, as is true in many of the other visor-like cap constructions, the resilient stay or stiffener member must be removed before the hat can be folded into a collapsed condition for storage.

SUMMARY OF THE INVENTION

Accordingly, it is an object of the present invention to provide for novel and improved headwear and particularly of the visor type which can be efficiently collapsed or coiled into a compact condition for storage when not in use.

It is another object of the present invention to provide for a novel and improved visor-type cap having a wire or wire-like reinforcing member which will establish the shape of the entire cap when worn and can be coiled with the cap into a compact package when not in use and will automatically return to its original shape or condition when placed on the head of the wearer.

A further object and feature of the present invention is to provide in a head covering for novel and improved reinforcing members which will serve as the sole means of shaping and support of the head covering and will remain a permanent part of the cap when laundered or folded for storage purposes without becoming misshapen, and further wherein the reinforcing members are so constructed and arranged that their characteristics will not be altered by laundering or cleaning of the cap, and will cause the cap to spring back to its desired shape when worn.

A still further object of the present invention is to provide for high strength, resilient reinforcing members for the bill and upper head-encircling portions of a cap which can be permanently inserted into the cap, are simple and inexpensive to manufacture and extremely rugged and durable in use.

In accordance with the present invention, a visor-like cap has been devised which is provided with the usual head-engaging or encircling portion, a visor extending form the head-engaging portion including a flexible, crescent-shaped section, and a first wire-like reinforcing member extending around the outer peripheral edge of the crescent-shaped section, the first reinforcing member including opposite ends terminating adjacent to said head-engaging portion, and the head-encircling portion defined by an annular section having an upper terminal edge, a second reinforcing member embedded in said terminal edge, said first and second reinforcing members each being composed of a wire or wire-like material having a memory and straightness such that when the cap is not worn it can be twisted into a coiled circular configuration of substantially reduced size in relation to its normal size when worn on the head of a wearer.

In the preferred form, the reinforcing members are comprised of preformed wire rope; i.e., helical strands of wire wrapped into a single cable. Preferably, the rope is encased in an outer flexible plastic sheath. In an alternate form, the reinforcing members are polyurethane cords either in the form of a solid rod or a tubular member having a circular cross-section and of a stiffness corresponding to that of the cable member described. In this relation, when used in combination with a head-encircling portion having free, releasably connectable ends, most desirably the head-encircling portion and the crescent-shaped section are composed of an essentially shapeless material, such as, a soft fabric so that the reinforcing members can be twisted into a tight coil. The free ends of the head-encircling portion are then wrapped several times with the free ends reattached to retain the cap in a compact bundle or package which can be easily stored in one's pocket or in a small bag and occupy very little space; yet, when the ends are released, the reinforcing members are sufficiently resilient that they will spring back into their original configuration. A particularly important and favorable characteristic of the reinforcing members is that they exhibit no tendency to kink even when compresed into a tightly coiled condition.

The above and other objects, advantages and features of the present invention will become more readily appreciated and understood from a consideration of the following detailed description of preferred and modified forms of the present invention when taken together with the accompanying drawings in which:

BRIEF DESCRIPTION OF THE DRAWINGS

FIG. 1 is a perspective view of a preferred form of cap in accordance with the present invention;

FIG. 2 is a side view in elevation of the form of cap illustrated in FIG. 1;

FIG. 3 is a front view in elevation illustrating the procedure for coiling the preferred form of cap shown in FIG. 1 into a compact storage position;

FIG. 4 illustrates the fully coiled configuration of the cap shown in FIGS. 1 to 3 for stowing in a bag;

FIG. 5 is a cross-sectional view taken about lines 5—5 of FIG. 1; and

FIG. 6 is another cross-sectional view taken about lines 6—6 of FIG. 1.

DETAILED DESCRIPTION OF THE PREFERRED EMBODIMENT

Referring in more detail to the drawings, there is illustrated in FIGS. 1 to 6 a preferred form of invention in the form of a cap 10 which is broadly made up of a head-encircling band 12 having a wire or wire-like reinforcing member 13 extending around its upper peripheral edge and a bill or visor 14 having a wire or wire-like reinforcing member 16 extending around the entire outer peripheral edge of the bill, an inner peripheral edge 20 of the bill being permanently attached to the band 12, such as, by suitable stitching, not shown. The style of cap 10 is given more as a setting for the present invention and is representative of numerous types of visor or cap constructions.

The head-encircling band 12 comprises inner and outer layers 18 and 19 of a fabric material defining a crown 22 above the visor 14 and terminating in an upper edge 21; and opposite sides of the band 12 taper rearwardly away from the crown 22 and terminate in free ends 23 and 24 which are releasably attached together as shown. Preferably, the inner layer 18 has its upper edge doubled over the reinforcing member 13 and seamed to the outer layer 19 as designated at 19' so as to surround and securely retain the reinforcing member 13 in position around the upper peripheral edge 21. Typically, the free ends 23 and 24 are releasably connected to one another by complementary Velcro fastening strips 23' and 24', as shown in FIG. 3, along the facing surfaces of the free ends 23 and 24 so that the ends may be connected to establish the proper fit.

The visor or bill 14 is of generally crescent-shaped configuration and is suitably made up of upper and lower fabric layers 26 and 27, respectively, and an intermediate layer of cotton batting or muslin 25 or other flexible or soft fabric material; and the layers 25-27, as shown in FIG. 4, are doubled over the reinforcing member 16 and seamed together as at 28 to closely surround and securely retain the reinforcing member 16 in position. An important feature of the present invention resides in the ability of the reinforcing members 13 and 16, by virtue of their composition and characteristics, to operate as the exclusive means of support and shaping of the band 12 and bill 14 when worn. Accordingly, when the ends 23 are 24 are connected together as described, the upper reinforcing member 13 will assume a generally circular or annular configuration so as t cause the band 12 not only to assume the same annular configuration but to lend a degree of stiffness to the band in a vertical direction, as illustrated in FIG. 2, to prevent the upper edge 21 from sagging or otherwise becoming misshapen. In a similar manner, the bill 14 will assume a generally upwardly convex configuration in a direction circumferentially across the inner peripheral edge 20, and the degree of convexity is progressively reduced in a radially outward direction toward the outer peripheral edge of the bill 14.

The reinforcing members 13 and 16 are preferably comprised of a preformed wire rope or helical strands of wire 30, and the strands are wrapped together and encased within a plastic sheath 32. A reinforcing material which lends itself particularly well for use in this application is that referred to as tiller cable and which is made up of galvanized or stainless steel wire strands coated with a vinyl or other plastic material. In the form shown, a 7×7 3/32" galvanized steel wire is coated with vinyl to 3/16", such as, Part No. 51820 manufactured and sold by Tie Down Engineering of Atlanta, Ga. The wire strands are wrapped or twisted together in the form of a helix which when encased within a vinyl sheath as at 32 possesses sufficient resiliency that it will bend into the configurations illustrated in FIGS. 1 and 2 when the cap 10 is placed in an encircling position around the head of the wearer. By forming the strands together into a single helix 30, the members 13 and 16 will not bend as easily as a single strand and will effectively resist any tendency to kink or crease when folded or coiled.

The inner peripheral edge of the bill 14 when secured to the band 12 will lend additional support or reinforcement to the cap when placed on the head, but the major reinforcement and support is provided by the member 16 and to the extent that the crescent-shaped layers 26 and 27 require no other shaping or supporting means, such as, cardboard, plastic or the like customarily used in conventional visor or cap constructions. In this relation, the reinforcing member 16, being constrained to follow the curved outline of the outer peripheral edge of the bill 14 possesses a sufficient degree of straightness or memory that it will exert a slight degree of tension on the fabric material of the bill 14 so as to maintain it in a taut or stretched condition; and in a like manner the reinforcing member 13 will maintain the fabric material of the band 12 in a somewhat stretched condition so as to avoid wrinkling or drooping of the band.

As further illustrated in FIGS. 3 and 4, the shapeless characteristics of the band 12 and bill 14 when combined with the limited resiliency of the reinforcing members 13 and 16 permit convenient folding or collapsing of the cap 10 into a compact package when not in use. Thus, by disengaging the free ends 23 and 24, the brim or outer peripheral edge of the bill 14 is twisted into a small loop or coil as designated at L. The free ends 23 and 24 of the band 12 are then wrapped around the loop L, as shown in FIG. 2, with the free end 23 facing in and the free end 24 facing out so that upon completion of wrapping can be secured together. This wrapping may be done in a single plane in surrounding relation to the loop or by wrapping over and under the loop while maintaining the loop in a tightly coiled condition. For instance, the free end 24 as shown in FIG. 3 would be wrapped in a clockwise direction around the loop, followed by wrapping the end 23 in an opposite direction, counterclockwise around the loop L and the partially wrapped free end 23 until the free end 24 moves into mating engagement with the end 23, essentially as shown in the completed condition in FIG. 3. FIG. 4 also illustrates a typical manner of storage of the cap by inserting the wrapped cap into a small bag or pouch B.

The reinforcing members 13 and 16 may be composed of other wire-like materials, such as, the extruded plastic cord as illustrated and described in my hereinbefore referred to application for U.S. Letters patent Ser. No. 650,236. Again, it is important that the members 13 and 16 possess sufficient resiliency or straightness as to be under a certain amount of tension tending to stretch the layers of material of the band 12 and bill 14 and yet be capable of being twisted or coiled into the storage position as described. It will therefore be appreciated that a novel and improved form of head covering has been devised in which the principal means of reinforcement of the band 12 and brim or visor 14 are wire or wire-like reinforcing members which will also serve to shape the head covering or cap when worn but nevertheless can remain permanently in place when laundered or folded for storage purposes without becoming misshapen. A wire cable as described has been found to be particularly effective by virtue of its combined resilience and stiffness, or straightness, for a given cross-sectional thickness, and that the members 13 and 16 can be twisted together into a tight coil without kinking or permanently bending.

It is therefore to be understood that various other modifications and changes may be made in the construction and arrangement of elements comprising the preferred and modified forms of invention as well as the composition of materials utilized without departing form the spirit and scope of the present invention as defined by the appended claims and reasonable equivalents thereof.

I claim:

1. A cap adapted for use as a head covering comprising in combination an upper, flexible head-encircling portion and a visor extending downwardly form said head-encircling portion, said visor including an unreinforced, flexible crescent-shaped section and a first elongated reinforcing member embedded in an outer peripheral edge of said section, said first reinforcing member including opposite ends terminating adjacent to said head-encircling portion, said head-encircling portion defined by an annular section having an upper peripheral edge, a second reinforcing member embedded in said upper peripheral edge, said first and second reinforcing members each composed of a wire or wire-like material having a straightness and memory such that when said cap is not worn said cap can be twisted into a tightly coiled, loop-shaped configuration of substantially reduced size in relation to its normal size when worn on the head of a wearer.

2. A cap according to claim 1, said second reinforcing member having a memory such that said head-encircling portion will assume a generally upright disposition above said visor when worn on the head of a wearer.

3. A cap according to claim 2, said head-encircling portion and said visor being capable of being manually twisted without kinking into a circular coil with said first and second reinforcing members coiled through greater than 360° into a coiled portion and with said opposite ends of said first and second reinforcing members overlapping said coiled portion.

4. A cap according to claim 1, said head-encircling portion having free, releasable connecting ends which when said visor is twisted into a coil are wrapped around said coil.

5. A cap according to claim 1, said first and second reinforcing members comprised of helical strands of wire, and a flexible sheath encircling said strands of wire.

6. A cap according t claim 5, said wire being a galvanized steel wire.

7. A cap according to claim 1, said crescent-shaped section and said upper head-encircling portion each composed of a shapeless material, such as, a soft fabric.

8. A cap according to claim 7, said head-encircling portion including inner and outer layers of a soft fabric material, said second reinforcing member interposed between said inner and outer layers, and a seam joining said inner and outer layers together in closely surrounding relation to said second reinforcing member.

9. A hat comprising in combination an upper, flexible head-encircling portion and a brim inclining downwardly from said head-encircling portion, said brim including an annular section and a first elongated reinforcing member embedded in an outer peripheral edge of said annular section, said first reinforcing member completely encircling said brim, said head-encircling portion defined by an upright annular section having an upper peripheral edge, a second reinforcing member embedded in said upper peripheral edge, said first and second reinforcing members each composed of a wire or wire-like section having a straightness and memory such that when said hat is not worn said hat can be twisted into a tightly coiled, loop-shaped configuration of substantially reduced size in relation to its normal size when worn on the head of a wearer, and said second reinforcing member having a memory such that said head-encircling portion will assume a generally upright disposition above said visor when worn on the head of a wearer.

10. A hat according to claim 9, said head-encircling portion and said brim being capable of being manually twisted without kinking into a circular coil with said firs and second reinforcing members coiled through greater than 360° into a coiled portion with said opposite ends of said first and second reinforcing members overlapping said coiled portion.

11. A hat according to claim 9, said head-encircling portion having free, releasable connecting ends which when said hat is twisted into a coil are wrapped around said coil.

12. A hat according to claim 9, said first and second reinforcing members each comprised of helical strands of wire, and a flexible sheath encircling said strands of wire.

* * * * *